United States Patent [19]
Flack et al.

[11] Patent Number: 6,114,397
[45] Date of Patent: Sep. 5, 2000

[54] GOSSYPOL FOR THE TREATMENT OF CANCER

[75] Inventors: Mary R. Flack, Kensington; Richard Knazek, Bethesda, both of Md.; Marcus Reidenberg, Scarsdale, N.Y.

[73] Assignee: The United States of America as represented by the Department of Health and Human Services, Washington, D.C.

[21] Appl. No.: 08/379,872

[22] Filed: Jan. 27, 1995

Related U.S. Application Data

[62] Division of application No. 07/551,353, Jul. 12, 1990, Pat. No. 5,385,936.

[51] Int. Cl.$^7$ .......................... A61K 31/12; A61K 31/11
[52] U.S. Cl. ........................................... 514/682; 514/700
[58] Field of Search ...................... 514/700, 682

[56] References Cited

PUBLICATIONS

Rao et al. (1985) *Cancer Chemother. Pharmacol.* 15:2–25.
Tanphaichitr et al. (1984) *Biology of Reproduction* 31:1049–1060.
Band et al., Gynecol. Oncol. (1989), 32(3), 273–7 (abstract only), 1989.
Rao et al, Cancer Chemother. Pharmacol, 15:20–25 1985.
Tso, Cancer Lett., 24: 257–261 1984.
Qian, Ann Rev Pharmacol, 24: 329–60 (1984).
Kim et al, Contraception 312 : 5966–72 (1984 .
Wu et al, Cancer Research 49, pp 3754–3758, Jul. 15, 1989.

*Primary Examiner*—Jerome D. Goldberg
*Attorney, Agent, or Firm*—Leydig, Voit & Mayer, Ltd.

[57] ABSTRACT

A method for treating cancer in a human, which comprises administering to the human subject an anti-cancer effective amount of a compound selected from gossypol, gossypol acetic acid, gossypolone, metabolites thereof, or physiologically acceptable salts thereof. Also included is a method for treating cancer in a human which comprises administering to the human subject an anti-cancer effective amount of any of the compounds listed above in combination with an anti-cancer effective amount of other conventional chemotherapeutic agents. Finally, the invention also encompasses a pharmaceutical composition comprising an anti-cancer effective amount of gossypol, gossypol acetic acid, or gossypolone, and an anti-cancer effective amount of a conventional chemotherapeutic agent, or combinations of the latter.

14 Claims, 2 Drawing Sheets

GOSSYPOL FOR THE TREATMENT OF CANCER

This application is a divisional of application Ser. No. 07/551,353, filed on Jul. 12, 1990, now U.S. Pat. No. 5,385,936, the entire contents of which are hereby incorporated by reference.

BACKGROUND OF THE INVENTION

1. Field of the Invention

The present invention is related to the use of gossypol and related compounds as anti-tumor agents effective against human cancers including, but not limited to, adrenocortical carcinoma, uterine, cervical, ovarian and testicular carcinoma, breast cancer, and carcinoid tumors.

2. Description of the Related Art

Gossypol is a double biphenolic compound derived from crude cottonseed oil which has been shown to inhibit spermatogenesis, and which has been used extensively as a male contraceptive in China.

While gossypol has been shown to retard the growth of some cancers in nude mice, its effects vary widely from species to species (Qian, S Z (1984) *Ann. Rev. Pharmacol. Toxicol.* 24: 329–60; Kim et al. (1984) *Contraception* 312: 5966–72). The effect of gossypol on the mitochondrial accumulation of rhodamine has been shown to be lower in magnitude in human cells than in rat testicular tumor cells (Tanphaichitr et al. (1984) *Biol. of Reprod.* 31: 1049–1060). Furthermore, closely related compounds such as mitotane (ortho-para'-DDD), a biphenolic compound which has been used to treat adrenal cancer, are only of limited effectiveness in treating cancer in humans. In addition, the side effects produced at the doses required for response can be debilitating, and include anorexia, nausea, vomiting, and dizziness. Conventional chemotherapy such as with cytoxan, adriamycin, 5FU, and other agents has a low response rate, and side effects such as hair loss, bone marrow suppression, nausea, vomiting, and heart failure. Clearly, an alternate or adjuvant therapy with less toxic side effects is desirable.

The use of gossypol and related compounds as anti-tumor agents against cancers in humans has yet to be reported.

SUMMARY OF THE INVENTION

The present invention relates to the use of compounds with the following formula:

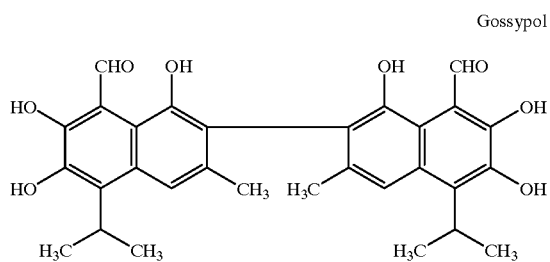

Gossypol in the treatment of human cancer, including treatment of adrenal, ovarian, thyroid, testicular, pituitary, prostate, and breast tumors, as well as other types of tumors.

Pharmaceutical compositions useful in the present method of treatment include the formulation of gossypol and gossypol acetic acid, which contain both the positive and negative enantamers of gossypol, and formulations containing only one enantamer, as well as any physiologically acceptable salts, for either enteral or parenteral use. Such compositions also include those containing gossypolone. These compounds may be used alone, in combination with one another, or in combination with other conventional chemotherapeutic pharmaceutical compositions. The invention also includes the use of any metabolic products generated from gossypol which have anti tumor activity.

As compared to conventional therapies, the use of gossypol and the related compounds noted above to treat human cancers is associated with milder side effects. These include mild fatigue, muscle tremor, dry mouth, dry skin, and occasional nausea. These are well tolerated, and patients are able to continue their normal activities. In addition, conventional chemotherapeutic agents are associated with a high degree of drug resistance. As discussed below, anti-tumor gossypol therapy has been demonstrated to be effective in patients who exhibit resistance to conventional anti-tumor agents.

As gossypol is taken up into a number of human endocrine tissues, including the adrenal gland, testis, ovary, uterus, thyroid and pituitary, it can be used in the treatment of cancers of these organs, and against carcinoid tumors which are tumors of neuroendocrine tissue which may be located in the lung, pancreas, or gastrointestinal tract.

As previously noted, gossypol has been found to retard the growth of some cancers in nude mice. However, its effects vary widely from species to species. It could not be assumed, therefore, that the anti-cancer effects seen in animals would be seen in humans. A further unexpected feature associated with the use of gossypol to treat cancer in human subjects as opposed to that in animals is that in the latter, higher doses of gossypol (e.g., 0.8 or 1.6 mg/mouse) have been shown to be lethal (Rao et al. (1985) *Cancer Chemother. Pharmacol.* 15: 20–25), negating any potential benefit of the drug in slowing cancer growth and prolonging survival. The present inventors have shown that the anti-tumor effect of gossypol in humans occurs at doses which are approximately one tenth of those effective in animals, i.e., 1 mg/kg/d vs. 10 mg/kg/d. Toxicity in humans begins to occur at doses greater than 1–2 mg/kg/d. Therefore, the studies of gossypol in animals do not make the use of gossypol for the treatment of cancer in humans, at appropriate doses, obvious in the latter.

Existing therapies for the treatment of human tumors, including adrenal, ovarian, thyroid, testicular, pituitary, prostate, and breast tumors, are multiple, including 5-fluorouracil, adriamycin, cytoxan, cisplatin, etoposide, suramin, and ortho-para'DDD (mitotane). These agents have a partial response rate of less than 20% for adrenocortical carcinoma, and less than 50% for other cancers. The toxicity of these agents, which is not exhibited by gossypol, includes myelosuppression, nausea, vomitting, anorexia, hair loss, cardiac failure and neurotoxicity. Thus, there is a need for anti-tumor agents with less toxicity which have activity against these tumors, and others, which are resistant to existing agents.

Gossypol is a human anti-tumor agent which causes fewer side effects than such existing treatments.

Accordingly, it is an object of the present invention to provide a method for treating cancer in a human, which comprises administering to the subject an anti-cancer effective amount of gossypol, gossypol acetic acid, or gossypolone.

Another object of the present invention is to provide a method for treating cancer in a human which comprises administering to the subject an anti-cancer effective amount of gossypol, gossypol acetic acid, or gossypolone, and an anti-cancer effective amount of 5-fluorouracil, adriamycin, cytoxan, cisplatin, etoposide, suramin, mitotane, or other conventional chemotherapeutic agent, or combinations of these compounds.

A further object of the present invention is to provide a pharmaceutical composition comprising an anti-cancer effective amount of gossypol, gossypol acetic acid, or gossypolone, and an anti-cancer effective amount of the compounds listed above, or combinations of these compounds.

Further scope of the applicability of the present invention will become apparent from the detailed description and drawings provided below. However, it should be understood that the detailed description and specific examples, while indicating preferred embodiments of the invention, are given by way of illustration only since various changes and modifications within the spirit and scope of the invention will become apparent to those skilled in the art from this detailed description.

BRIEF DESCRIPTION OF THE DRAWINGS

The above and other objects, features, and advantages of the present invention will be better understood from the following descriptions taken in conjunction with the accompanying drawings, in which.

DETAILED DESCRIPTION OF THE INVENTION

Media, Reagents, and Cells

Dulbecco's minimal Eagle's medium, fetal calf serum, glutamine, penicillin, and streptomycin were purchased from Quality Biological, Inc. (Gaithersburg, Md.); Hanks' balanced salt solution and trypsin-EDTA were obtained from Gibco Laboratories (Grand Island, N.Y.). 1,6-Diphenylhexatriene and tetrahydrofuran were from Aldrich Chemical Co., Inc. (Milwaukee, Wis.). Gossypol and gossypol acetic acid were gifts from the National Research Institute for Family Planning (Beijing, China). The established line of small cell human adrenocortical carcinoma (SW-13) was purchased from the American Type Culture Collection (Rockville, Md.).

In Vitro Gossypol Treatment
Cell Proliferation

SW-13 cells were seeded in a 25-$cm^2$ tissue culture flask (Costar, Cambridge, Mass.) at densities of $1 \times 10^4$ cells/5 ml of Dulbecco's minimal Eagle's medium, supplemented with 10% fetal calf serum, 100 ug/ml streptomycin, 100 units/ml penicillin, and 2 mM glutamine. The cells were grown in a humidified, 37° C. incubator with a 5% $CO_2$/95% air atmosphere. A gossypol stock solution in absolute ethanol was added to the culture medium to yield final concentrations of 0, 0.5, 5, and 50 uM gossypol with a 0.1% final ethanol concentration. After 1, 2, 4, or 6 days of incubation, the culture medium containing a few floating cells was removed. Adherent cells were trypsinized (0.1% trypsin, w/v) and counted using a hemocytometer. Cell viability was determined by trypan blue exclusion.

Figure 1:
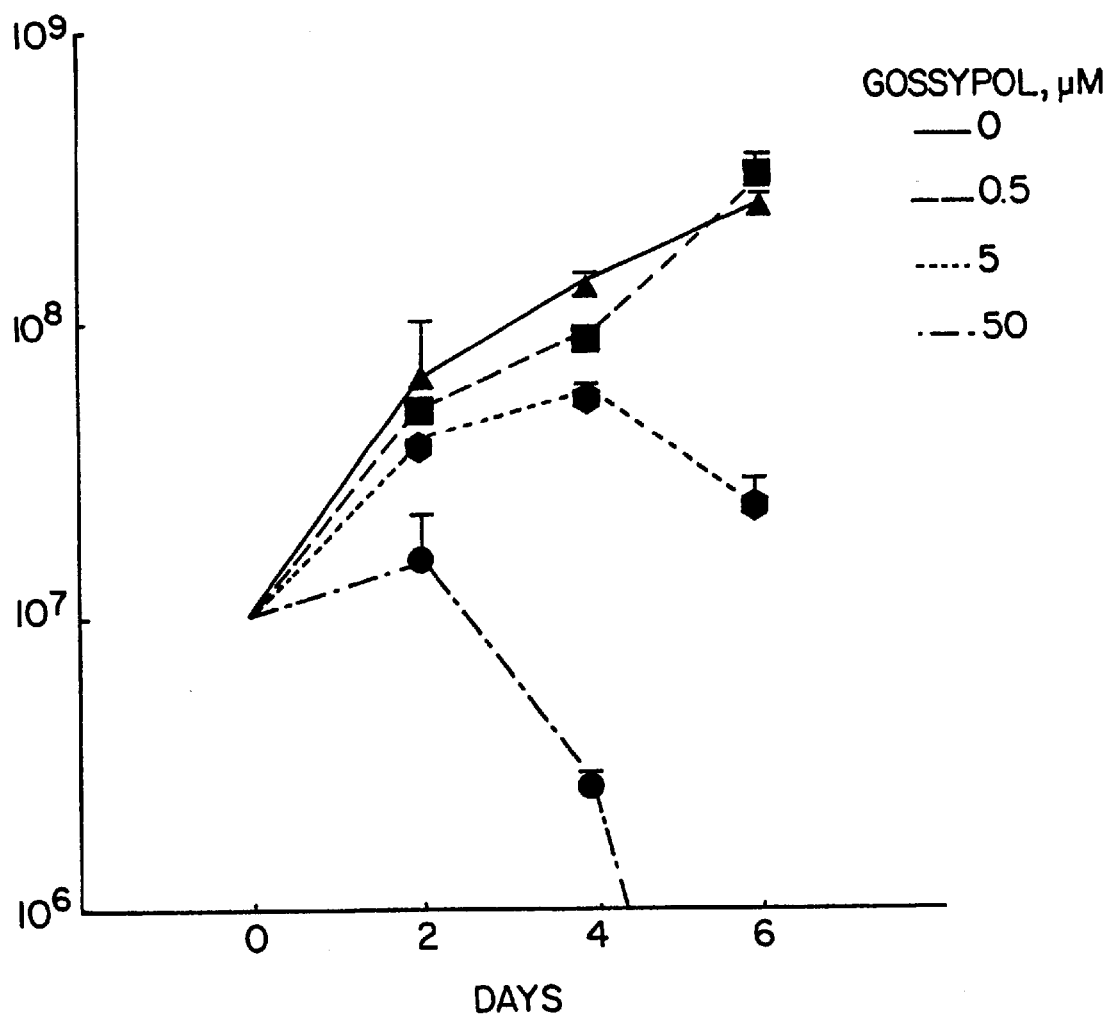
FIG. 1 shows the effects on proliferation of SW-13 cells of 0, 0.5, 5, and 50 uM gossypol during prolonged exposure. SW-13 cells were seeded ($1 \times 10^4$ cells) into 25 $cm^2$ tissue culture flasks in Dulbecco's minimal Eagle's medium supplemented with fetal calf serum (10%), 100 ug/ml streptomycin, 100 units/ml penicillin, and 2 mM glutamine. Exposure to 5 and 50 uM gossypol inhibited cell proliferation.

As shown in FIG. 1, exposure of SW-13 cells to 5 and 50 uM gossypol inhibited cell proliferation.

In Vivo Gossypol Treatment
Nude Mice

Nude mice (Charles River, Kingston, N.Y.) weighing 20–35 g were caged in a temperature-controlled (26–28° C.), 12 h/12 h light/dark animal room. A microporous cage bonnet served as an effective protective barrier between the animal and the outside environment. In addition, the room was continuously purged with High Efficiency Particle Attenuator-filtered air. The cages, feeders, and water bottles were designed to make standard mouse chow and water readily available while minimizing the opportunity for the transfer of communicable pathogens.

Transplantation of SW-13 Cells

Forty-nine adult male nude mice weighing 20–24 g were divided into two groups of 24 for control and 25 for gossypol treatment. Gossypol acetic acid was suspended in 75% ethanol for 24 h, then evaporated in vacuum chamber with desiccant, and finally suspended in sterilized 0.25% carboxymethylcellulose carrier. The gossypol-treated group received 30 mg gossypol/kg body weight/day via an orogastric tube. Control mice were fed an equal volume of carrier. Body weights were measured weekly. At the end of the first week of gossypol treatment, $2 \times 10^6$ SW-13 cells were injected s.c. on the back of these mice, which continued to receive gossypol or carrier for 5 additional weeks. Tumor surface areas (length×width, $cm^2$) were measured daily. After 5 weeks, the animals were decapitated.

Another experiment was designed wherein 48 adult male nude mice weighing 25–35 g were injected s.c. with $2 \times 10^6$ SW-13 cells. One month later, the animals were divided into two groups of 24. There were 7 nude mice without visible tumors in each group. The gossypol treated animals received 30 mg gossypol acetic acid/kg body weight/day whereas control animals were fed an equal volume of carrier. Body weights and tumors sizes (lengths×width, $cm^2$) were measured weekly. During the 12th week of treatment, 5 control animals died. Since it appeared unlikely that the remaining control animals would survive for another week, they were then sacrificed. Autopsies were performed on all animals including those that died during the study period. Internal organs were examined for the presence of gross tumor.

Statistical Analysis

Data are expressed as the mean±SD unless otherwise indicated. Statistical comparisons were made using an unpaired Student's t test.

Effect of Gossypol on SW-13 Tumor Bearing Nude Mice

In this experiment, nude mice had been given s.c. injections of SW-13 adrenocortical carcinoma 1 month prior to initiation of the treatment with either gossypol or carrier.

During the subsequent 12 weeks of treatment, there were 10 deaths in the control group: 4 had apparent ascites, were jaundiced, and had large intraperitoneal tumors; 2 suffered from hind leg paralysis due to a tumor metastatic to the spinal column; 2 animals had small tumors, but both showed significant weight loss; 2 had demonstrated neither visible tumors nor an obvious cause of death. In contrast, only two deaths were observed in the gossypol-treated group, one of them having ascites while the other had no apparent tumor at autopsy. Each treated mouse in the group received a total dose of 81.9 mg gossypol during the 12-week period.

As in the previous study, 12 weeks of gossypol treatment had no signficant effect on body weights. At the end of the study period, the body weights in both groups were 32.2±3.8 and 30.9±3.6 g for the control and gossypol-treated groups, respectively. After 12 weeks of treatment, the tumor prevalence had risen from 71 to 83% in the control group, while the gossypol-treated group exhibited a decrease in tumor prevalence from 71% to 54%. This was accompanied by the death of 41.6% of the controls and 8.3% of the gossypol-treated group (Table 1).

TABLE 1

Effect of gossypol on tumor prevalence and mortality in mice having preexisting tumors

| Week | Control (%) | | Gossypol (%) | |
|---|---|---|---|---|
| | Prevalence of tumor | Total deaths | Prevalence of tumor | Total deaths |
| 0 | 71 | 0 | 72 | 0 |
| 1 | 75 | 0 | 63 | 0 |
| 2 | 83 | 0 | 50 | 0 |
| 3 | 83 | 0 | 54 | 0 |
| 4 | 83 | 0 | 50 | 0 |
| 5 | 83 | 0 | 58 | 0 |
| 6 | 83 | 0 | 58 | 0 |
| 7 | 83 | 8.3 | 58 | 0 |
| 8 | 83 | 8.3 | 58 | 0 |
| 9 | 83 | 12.5 | 54 | 0 |
| 10 | 83 | 16.7 | 54 | 0 |
| 11 | 83 | 20.8 | 54 | 0 |
| 12 | 83 | 41.6 | 54 | 8.3 |

The mean tumor sizes of the control and the gossypol treated groups were shown as a function of duration of treatment in Table 2. The slight decline in the mean tumor size observed towards the end of the study period was due to the fact that the majority of the control mice that died during the study had large tumors.

TABLE 2

Effect of gossypol on mean tumor size

| | Mean tumor size ($cm^2$) (mean ± SE) | |
|---|---|---|
| Week | Control | Gossypol |
| 0 | 0.09 ± 0.02 | 0.08 ± 0.02 |
| 1 | 0.22 ± 0.05 | 0.07 ± 0.02 |
| 2 | 0.28 ± 0.06 | 0.11 ± 0.04[a] |
| 3 | 0.35 ± 0.07 | 0.15 ± 0.05[a] |
| 4 | 0.50 ± 0.11 | 0.20 ± 0.07[a] |
| 5 | 0.66 ± 0.17 | 0.28 ± 0.08[a] |
| 6 | 0.87 ± 0.22 | 0.32 ± 0.10[a] |
| 7 | 0.97 ± 0.25 (n = 23) | 0.38 ± 0.12[a] |
| 8 | 1.16 ± 0.33 (n = 22) | 0.45 ± 0.14[a] |

TABLE 2-continued

Effect of gossypol on mean tumor size

| | Mean tumor size ($cm^2$) (mean ± SE) | |
|---|---|---|
| Week | Control | Gossypol |
| 9 | 1.07 ± 0.34 (n = 20) | 0.50 ± 0.15[a] |
| 10 | 1.14 ± 0.36 (n = 20) | 0.59 ± 0.18[a] |
| 11 | 1.39 ± 0.41 (n = 19) | 0.68 ± 0.21[a] |
| 12 | 0.96 ± 0.21 (n = 15) | 0.81 ± 0.25 (n = 22) |

[a]$P < 0.05$, control compared to gossypol treated group; n = 24 unless otherwise indicated.

Figure 2:
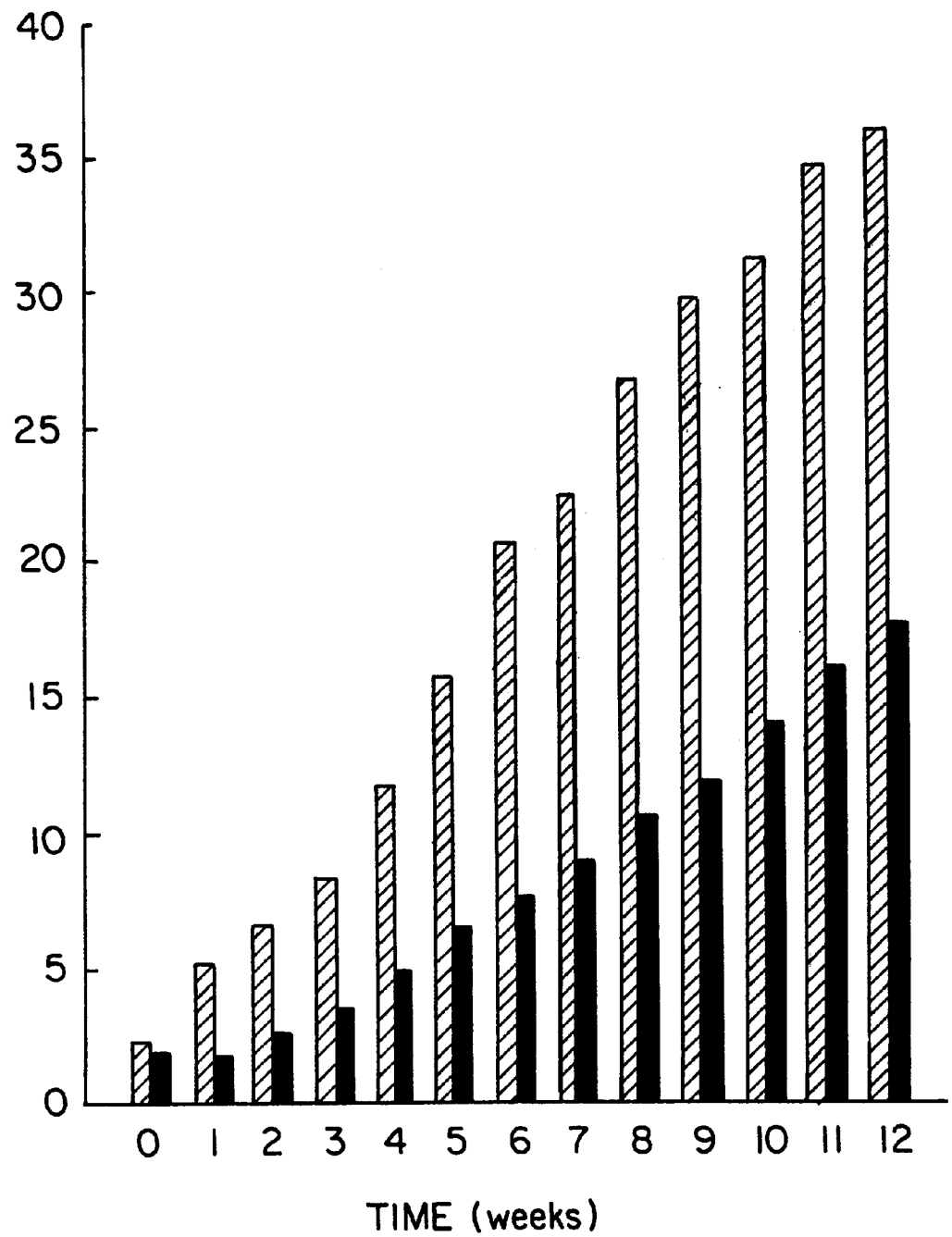
FIG. 2 shows the effect of gossypol on the cumulative surface area of SW-13 human adrenocortical carcinoma in nude mice. Gossypol and placebo were given one month after the injection of tumor cells. Gossypol (mg/kg/day): ■, ○; ■, 30.

The total tumor burden of the two groups rose during the treatment period, the controls reaching a value twice that of the gossypol group at the 12th week (FIG. 2).

Treatment of Human Metastatic Adrenal Cancer

Previous medical therapy for metastatic adrenocortical carcinoma has been largely unsuccessful. Based on the growth inhibitory effect of gossypol on SW-13 human adrenocortical tumors in vivo in nude mice, discussed above, the effect of oral gossypol treatment on metastatic adrenal cancer in a human patient was investigated.

A 36 year old man presented with a left sided adrenocortical carcinoma, 26×13 cm, invading the kidney and inferior vena cava. Surgical excision of all visible tumor was performed, and the patient was started on mitotane postoperatively. Pulmonary metastases were found six months later, which were resected. Six month following thoracotomy, multiple hepatic metastases were found. His tumor progressed despite treatment with Suramin and adriamycin/VP16.

At the time of gossypol treatment, the patient had nocturnal dyspnea requiring supplemental oxygen therapy, markedly decreased exercise tolerance, persistent abdominal pain, and pedal edema. Physical examination revealed a cushingoid man with a blood pressure of 150/90, bilateral tender gynecomastia, a liver span of 14 cm, abdominal distention and fluid wave, and bilateral pitting edema to the knee.

Gossypol acetic acid, 10 mg compressed tablet, was given orally at a dose of 20 mg/d which was increased by 10 mg/d every three days to a dose of 50 mg/d.

During gossypol treatment, the patient experienced fatigue, xerostomia, tremor, and transaminitis. After three weeks of gossypol treatment, CT scans showed complete resolution of pulmonary metastases and greather than 50% decrease in the size of the hepatic metastases, and an improvement in abdominal pain, ascites, and pulmonary function.

A summary of the results obtained in this and other human subjects during a phase I clinical trial of oral gossypol for the treament of metastatic adrenocortical carcinoma is presented in Table 3.

TABLE 3

Summary of Preliminary Results of Phase 1 Clinical Trial of Oral Gossypol for Adrenocortical Cancer

| Age/Sex | Site | Dose | Duration | Level | Side Effects | Response |
|---|---|---|---|---|---|---|
| 36/M* (*Patient described above) | Lung Liver | 40–60 mg/d | 28 weeks | 463 ng/dl | Xerostomia Fatigue Gynecomastia Transaminitis | Partial Response |

TABLE 3-continued

Summary of Preliminary Results of Phase 1 Clinical Trial of Oral Gossypol for Adrenocortical Cancer

| Age/Sex | Site | Dose | Duration | Level | Side Effects | Response |
|---|---|---|---|---|---|---|
| 26/M | Lung Liver | 70 | 3 weeks | 1,025 | Xerostomia Nausea Transaminitis | Progression |
| 52/F | Abdomen | 40 | 6 weeks | 444 | Xerostomia Fatigue Nausea | Partial Response |
| 34/M | Abdomen Liver | 40–50 | 12 weeks | 291 | Xerostomia Fatigue Nausea | Stabilization |
| 27/M | Abdomen Pelvis | 50 | 6 weeks | 229 | Xerostomia Fatigue | Progression |

Of these five patients, two exhibited partial tumor responses, one has stable disease, and two showed tumor progression.

Pharmaceutical Compositions and Modes of Administration of Gossypol and Related Compounds The method of the present invention includes the administration of gossypol, gossypol acetic acid, or gossypolone, alone or in combination with one another and/or other conventional chemotherapeutic agents, and a pharmaceutically acceptable excipient, to a human subject.

In the methods according to the present invention pharmaceutical compositions containing compounds according to the present invention are administered in an effective amount to a human host for the treatment of a variety of human cancers including adrenal, ovarian, thyroid, testicular, pituitary, prostate, and breast cancer.

In administering gossypol and related compounds for the treatment of cancer by the methods of the present invention, certain pharmaceutical compositions, doses, routes of administration, and desired blood levels may be employed. These are summarized in the table below. In each case, the indicated dose and blood level are approximate, e.g., for oral administration of gossypol acetic acid(+)-compressed tablet, the dose may be from about 40 to about 100 mg/d, and the desired blood level may be from about 400 to about 800 ng/dl.

TABLE 4

Pharmaceutical Formulations, Doses, Routes of Administration, and Effective Blood Levels of Gossypol and Related Compounds for the Treatment of Human Cancer.

| Formulation | Route | Dose | Blood Level |
|---|---|---|---|
| Gossypol acetic acid (+)—compressed tablet | Oral | 40–100 mg/d | 400–800 ng/dl |
| Gossypol acetic acid (+)—suppositories | Rectal, vaginal | 40–140 mg/d | 400–1000 ng/dl |
| Gossypol(+)—PVP and physiologic salts | Parenteral | 1–2 mg/kg/d | 400–1000 ng/dl |
| Gossypol acetic acid (±)—compressed tablet | Oral | 40–100 mg/d | 400–800 ng/dl |
| Gossypol acetic acid (±)—suppositories | Rectal, vaginal | 40–140 mg/d | 400–1000 ng/dl |
| Gossypol(±)—PVP and physiologic salts | Parenteral | 1–2 mg/kg/d | 400–1000 ng/dl |
| Gossypol(−)—tablet | Oral | 20–100 mg/d | 200–1000 ng/dl |
| Gossypol(−)—suppositories | Rectal | 40–140 mg/d | 200–1000 ng/dl |
| Gossypol(−)—PVP and physiologic salts | Parenteral | 1–2 mg/kg/d | 200–1000 ng/dl |
| Gossypolone tablet | Oral | 50–200 mg/d | 400–1000 ng/dl |
| Gossypolone suppositories | Rectal, vaginal | 50–200 mg/d | 400–1000 ng/dl |
| Gossypolone PVP and physiologic salts | Parenteral | 1–5 mg/kg/d | 400–1000 ng/dl |

When administered orally, the drug may be taken in divided doses, two to three times a day.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed:

1. A method for treating a cancer in a human, wherein the cancer is susceptible to treatment with gossypol, a physiologically acceptable salt of gossypol, gossypolone, a physiologically acceptable salt of gossypolone, or any combination thereof, which method comprises:

administering to said human an anti-cancer effective amount of at least one compound selected from the group consisting of gossypol, a physiologically acceptable salt of gossypol, gossypolone, and a physiologically acceptable salt of gossypolone, and a pharmaceutically acceptable carrier.

2. The method of claim 1, wherein said cancer is adrenal, ovarian, thyroid, testicular, pituitary, prostate, or breast cancer.

3. The method of claim 2, wherein said cancer is adrenal cancer.

4. The method of claim 1, wherein the blood concentration of said compound is 400–1000 ng/dl.

5. The method of claim 4, wherein said compound is gossypolone or a physiologically acceptable salt of gossypolone.

6. The method of claim 5, wherein said gossypolone or physiologically acceptable salt of gossypolone is administered orally, rectally or vaginally at a dose of 50–200 mg/d.

7. The method of claim 5, wherein said gossypolone or physiologically acceptable salt of gossypolone is administered parenterally at a dose of 1–5 mg/kg/d.

8. A method for treating a cancer in a human, wherein the cancer is susceptible to treatment with gossypol, a pharmaceutically acceptable salt of gossypol, or a combination thereof, which method comprises:

administering to said human an anti-cancer effective amount of at least one compound selected from the group consisting of gossypol and a physiologically acceptable salt thereof, and a pharmaceutically acceptable carrier.

9. The method of claim 8, wherein said cancer is adrenal, ovarian, thyroid, testicular, pituitary, prostate or breast cancer.

10. The method of claim 8, wherein said cancer is adrenal cancer.

11. The method of claim 8, wherein the blood concentration of said compound is 400–1000 ng/dl.

12. The method of claim 8, wherein said compound is administered parenterally at a dose of 1–2 mg/d.

13. The method of claim 8, wherein said compound is administered orally at a dose of 20–100 mg/d.

14. The method of claim 8, wherein said compound is administered rectally at a dose of 40–140 mg/d.

* * * * *